US011883205B2

(12) United States Patent
Refsnæs et al.

(10) Patent No.: US 11,883,205 B2
(45) Date of Patent: Jan. 30, 2024

(54) SUPPORT STRUCTURE

(71) Applicant: ABLY MEDICAL AS, Ålesund (NO)

(72) Inventors: Jørn Refsnæs, Ålesund (NO); Arve Voldsund, Leinøy (NO); Cato Alexander Bjørkli, Hvalstad (NO); Leila Yousif Circhirillo, Oslo (NO); Kjell Are Furnes, Nesoddtangen (NO)

(73) Assignee: Ably Medical AS, Alesund (NO)

(*) Notice: Subject to any disclaimer, the term of this patent is extended or adjusted under 35 U.S.C. 154(b) by 0 days.

(21) Appl. No.: 17/050,500

(22) PCT Filed: Apr. 29, 2019

(86) PCT No.: PCT/EP2019/060985
§ 371 (c)(1),
(2) Date: Oct. 26, 2020

(87) PCT Pub. No.: WO2019/207169
PCT Pub. Date: Oct. 31, 2019

(65) Prior Publication Data
US 2021/0128065 A1    May 6, 2021

(30) Foreign Application Priority Data
Apr. 27, 2018    (GB) .................................. 1806938

(51) Int. Cl.
A61B 5/00    (2006.01)
A61B 5/11    (2006.01)
G01L 1/16    (2006.01)

(52) U.S. Cl.
CPC .......... A61B 5/6891 (2013.01); A61B 5/1116 (2013.01); G01L 1/16 (2013.01);
(Continued)

(58) Field of Classification Search
CPC .... A61B 2562/0247; A61B 2562/0261; A61B 5/1116; A61B 5/6891; A61B 5/6892; A61G 2203/36
See application file for complete search history.

(56) References Cited

U.S. PATENT DOCUMENTS

2004/0111045 A1*  6/2004  Sullivan ............... A61B 5/6892
                                                   600/595
2009/0294257 A1   12/2009  Kuiper et al.
2010/0005587 A1*  1/2010  Choi .................... A47C 19/122
                                                   5/202
(Continued)

FOREIGN PATENT DOCUMENTS

CN    100592892 C    3/2010
CN    103728056 A    4/2014
(Continued)

OTHER PUBLICATIONS

International Preliminary Report on Patentability dated Apr. 20, 2020 in connection with International Patent Application No. PCT/EP2019/060985, 6 pages.
(Continued)

Primary Examiner — Etsub D Berhanu
Assistant Examiner — Michael A Catina
(74) Attorney, Agent, or Firm — Dorsey & Whitney LLP

(57) ABSTRACT

There is provided an apparatus comprising one or more resilient members for supporting a human or other animal, wherein the one or more resilient members each comprise one or more sensor elements that are attached to and run at least partially along the length of the respective resilient member, and each of the one or more sensor elements is configured to provide an electrical response proportional to the amount of movement of the respective resilient member.

18 Claims, 6 Drawing Sheets

(52) U.S. Cl.
CPC ............. *A61B 5/6894* (2013.01); *A61B 5/746* (2013.01); *A61B 2562/0219* (2013.01); *A61B 2562/0247* (2013.01); *A61B 2562/0261* (2013.01); *A61B 2562/043* (2013.01)

(56) References Cited

U.S. PATENT DOCUMENTS

| | | | |
|---|---|---|---|
| 2010/0094139 A1* | 4/2010 | Brauers | A61B 5/6887 600/595 |
| 2017/0135881 A1 | 5/2017 | Franceschetti et al. | |
| 2017/0135883 A1* | 5/2017 | Franceschetti | G05B 19/042 |
| 2017/0251823 A1 | 9/2017 | Nakamura et al. | |

FOREIGN PATENT DOCUMENTS

| | | |
|---|---|---|
| CN | 103930026 A | 7/2014 |
| EP | 0294927 A1 | 12/1988 |
| GB | 2319851 A | 6/1998 |
| TW | 333044 U | 6/1998 |
| WO | 2004045407 A1 | 6/2004 |
| WO | 2007074800 A1 | 7/2007 |
| WO | 2018083566 A1 | 5/2018 |

OTHER PUBLICATIONS

Office Action dated Sep. 1, 2021 in connection with Chinese Patent Application No. 201980042065.3, 12 pages including English translation.

International Search Report and Written Opinion dated Sep. 16, 2019 in connection with PCT/EP2019/060985, 8 pages.

Office Action dated Apr. 20, 2022 in connection with Chinese patent application No. 2019800420653, 4 pages Including English translation.

* cited by examiner

SUPPORT STRUCTURE

This application is a national stage application under 35 U.S.C. § 371 of International Application No. PCT/EP2019/060985, filed Apr. 29, 2019, entitled SUPPORT STRUCTURE, which claims priority to U.K. Patent Application GB 1806938.5, filed Apr. 27, 2018.

FIELD OF THE INVENTION

The present disclosure relates generally to resilient members that can be used to sense movement along the length of the member. Particular applications include the use of a plurality of sensor elements (e.g., a piezoelectric material) in a structure configured to support a person or other animal (i.e., a "support structure"). The support structure may form part of a larger device for this purpose, for example a bed or seat (e.g., wheelchair seat). In such applications, the resilient members may be used to sense changes in one or more of pressure, acceleration, strain, or force.

BACKGROUND

Sensors have been used to detect the position of a person that is resting, sitting or lying on a support structure, such as a bed. However, the range of sensors used to detect the position of a person on a bed is currently wide-ranging. In most applications, too much emphasis has been placed on the accuracy of each particular sensor. For example, position sensors may be able to accurately determine the exact position of a patient lying on a bed, but they will not be of any use in determining breathing motion or heart rate.

Sensors have been incorporated into support structures, but usually are provided in the form of mats or pads. Whilst the response of these sensors can provide some information, further improvement is needed to permit such sensors to respond better to the typical movement of a patient.

The present invention aims to address these deficiencies in current support structures and also improve sensor elements in general.

SUMMARY

In accordance with the broadest aspects of the invention, there is disclosed a resilient member in the form of an elongate member, e.g., in the form of a tube, wherein one or more sensor elements extend along the length of the member for sensing changes in movement of the resilient member. The sensor element is configured to output an electrical response proportional to the amount of movement of the elongate member. The sensor element may be configured to generate an electrical charge, current or voltage resulting from a mechanical force applied to the resilient member. The charge, current or voltage may be proportional to the amount of mechanical force applied to the resilient member. In various embodiments the sensor element comprises a piezoelectric material extending along the length of the tube.

The use of a sensor element that is configured to output an electrical response proportional to the amount of movement of the elongate member allows measurement of any force related to movement to be measured. More specifically, the measured movement could be movement due to changes in one or more of pressure, acceleration, strain, or any other force that causes movement of the elongate member.

As used herein, resilience may be defined as capable of springing back into shape after being moved, e.g., bent, stretched or squashed. The piezoelectric, resilient member may have a homogenous or progressive resilience throughout its length. This resilience may be provided by a portion of the member comprising a resilient element. For example, the member may be made up of a number of component parts, one of which comprises a resilient piece extending along the length of the member. The resilient piece could be made of, e.g., spring steel or glass-reinforced plastic ("GFK"). The resilience (or stiffness) of the members would be tailored for the intended use, but typically is sufficient to support a human or other animal.

In accordance with aspects of the invention, there is provided an apparatus comprising one or more elongate, resilient members for supporting a human or other animal, wherein the one or more resilient members each comprise one or more sensor elements that are attached to and run at least partially along the length of the respective resilient member, and each of the one or more sensor elements is configured to provide an electrical response proportional to the amount of movement of the respective resilient member.

The sensor elements may be configured to generate an electrical charge, current or voltage resulting from a mechanical force applied to the resilient member. The charge, current or voltage may be proportional to the amount mechanical force applied to the resilient member.

The sensor elements described herein are not necessarily aimed at sensing the movement of a person to determine their exact position, for example. Rather, the sensor elements disclosed herein seek a trade-off. In many applications, for example, it is not necessary to know exactly how or where a patient is positioned, but instead determine certain motions of the patient, from which information can be ascertained from a single type of sensor (in this case one that is attached to the resilient member).

Thus, the sensor elements disclosed herein run at least partially along the length of the respective resilient member, and can respond to changes in movement, e.g. a patient moving from one side to another, or having a seizure, as well as smaller movements such as heart rate, how the patient is breathing, abdomen noises from the stomach/intestine and so forth.

The sensor element may, for example, be a piezoelectric material. This would run along the length of the sensor as mentioned above, but would typically not have a resolution in the lengthwise direction. What can be quite important, however, is whether the patient is moving side-to-side, or thrashing about, etc. and use of a piezoelectric material would be particularly advantageous in these situations. This is particularly the case when attaching multiple piezoelectric sensor elements to each of the resilient members that are in a parallel array.

The one or more sensor elements may each be attached to a respective elongate, resilient member at least partially along its length. For example, the sensor elements may be encased by or embedded in a respective resilient member as discussed below, or the sensor element may be attached (e.g., adhered) to the respective resilient member, for example an outer surface thereof. This means the sensor element may generally follow the longitudinal profile of the elongate, resilient member. As such the sensor elements may respond to changes in the longitudinal profile of the elongate, resilient member (using the aforesaid electrical response). This is seen as particularly advantageous when the one or more elongate, resilient members are used to provide the main supporting element/function for the support structure, as described herein, since the sensor elements respond directly to movement of the main supporting element of the structure. Simply inserting a pad (even a resilient one) within a mattress does not achieve this, for example, since the sensor elements in this case are not in direct contact with the resilient elements of the mattress (i.e., the springs), which provide the main supporting function.

A particular sensor element incorporating a piezoelectric material that could be used in the present invention is "PIEZO COPOLYMER COAXIAL CABLE" (Internal number CAT-PFS0002) manufactured by TE Connectivity.

In various embodiments the resilient members could comprise one or more materials intended to impart a particular quality (e.g., stiffness and/or resilience and/or tensile strength). For example, the one or more materials could be one or more of glass reinforced plastic or fiberglass ("GFK"), spring steel, and composite materials. As discussed below the stiffness and/or resilience and/or tensile strength of the resilient members may vary or be variable along their length.

The technology disclosed herein, in particular the use of movement sensors attached to and running along the length of supporting resilient members, is seen as an improvement over conventional arrangements.

Each of the one or more elongate, resilient members may have a central, longitudinal axis, and a length defined along the central, longitudinal axis that is at least 10, 20 or 50 times a width of the resilient member, wherein the width is defined as a lateral dimension (e.g., the largest lateral dimension) of the resilient member that extends through its central, longitudinal axis. The elongate resilient members may be long and/or thin and/or narrow and/or slender.

The invention may also provide a support structure comprising a plurality of resilient members as described above. The resilient members may be arranged substantially parallel to each other and/or in an array across the support structure. Each resilient member may comprise a separate sensor element configured to provide an electrical response proportional to the amount of movement of that respective resilient member. Such an arrangement may be used to sense movement or other characteristics of a person located on the support structure, by sensing changes in one or more of pressure, acceleration, strain, or force using the piezoelectric members.

The use of a parallel array of elongate resilient members is seen as particularly advantageous, especially in the case of a bed, since this permits an improved response to movements of the patient, e.g., in a transverse/lateral direction to the parallel array.

The resilient members may be substantially fixed against transverse/lateral (e.g., side-to-side) movement, for example when they are located in a parallel array.

The support structure may be configured to support a person or other animal, and/or may be part of a device configured to support a person or other animal, for example the device may be a bed (e.g., a hospital or medical bed), seat (e.g., a chair, wheelchair or other medical seat) or other supporting device. The resilient members described herein may be used in any application in which a human or animal is being supported, for example a transporting device (e.g., a vehicle) could comprise one or more support structures utilising elongate, resilient members as described herein.

Each resilient member may extend from a first end of the support structure to a second, opposite end of the support structure. In this manner, in some embodiments each resilient member may extend along substantially an entire length or width of the support structure. In other embodiments, the sensor elements may run only partially along the length or width of each resilient member. For example, in the case of a bed the sensor elements may run along the length of the resilient members that corresponds to the torso region. This enables detection of vital signs, movement, respiration, etc. whilst conserving the material used for the sensor elements. Running the sensor elements along substantially the entire length can be beneficial, however, since this enables a larger range of movements to be detected. A lot of movements of a patient start at the arms, legs or even feet, and so this movement is picked up efficiently by the sensors if they extend along substantially the entire length.

The one or more resilient members may be configured to support a human or other animal that rests (e.g., sits or lies) on the support structure. The members may be configured to deform slightly due to the weight of the human or other animal resting on the structure, but may spring back into substantially their original shape and/or position once the human or other animal is no longer resting on the support structure. In this manner the resilient members may be the main supporting element (and/or provide the primary support) for a person or other animal on the support structure. That is, the support structure may rely on the resilient members in order to adequately support a human or other animal in use. This distinguishes the resilient members described herein from parts of a support structure that may have some resilience, but do not contribute to supporting a human or other animal in use.

A person of skill in the art would understand that the resilience or stiffness of the members required to achieve the above function would depend on many factors that are specific to the intended application. However, the skilled person would generally be aware of the level of stiffness or resilience required in any particular application.

The one or more resilient members may comprise at least 5, 6, 7, 8, 9 or 10 resilient members, each comprising a separate sensor element configured to provide an electrical response proportional to the amount of movement of the respective resilient member.

A particularly advantageous arrangement, that may be claimed independently, is a support structure for a chair or bed that has a plurality of (e.g., at least 5, 6, 7, 8, 9 or 10) elongate, resilient members arranged in a parallel array across the support structure as described above, wherein a separate sensor element is attached to each (or at least some) of the elongate, resilient members in such a manner that means the sensor element follows the longitudinal profile of the elongate, resilient member, wherein the resilient members are the main supporting element (and/or provide the primary support) for a person or other animal on the support structure. This has been found to provide a support structure that can reliably support the human or other animal whilst providing a decent trade-off as described above and avoiding the need for, e.g., sensor mats, pads or other similar devices to be placed within or beneath a mattress. As described above, the sensor elements are also better equipped to respond to movement changes in the human or animal since they respond directly to the movement of the main supporting element.

In any of the aspects and embodiments described herein, each of the one or more resilient members may comprise a sheath, for example an outer sheath at least partially (or fully) encases a respective one of the sensor elements. This can protect the sensor elements in use and increases their accuracy.

Each of the sensor elements may be embedded in a respective one of the resilient members. For example, each sensor element could be embedded into a groove of a respective one of the resilient members. The groove could extend from an outer (e.g., upper) surface of each resilient member. To maximize the response of the sensor element the groove could be located in an upper surface of the resilient member configured to face the person or animal in use.

Each of the one or more resilient members may further comprise one or more resilient support elements that run at least partially along the length of the resilient member, wherein the one or more resilient support elements may be configured to support the respective sensor element of the resilient member.

The strength and/or stiffness and/or resilience of each of the resilient members could be varied or variable along their length. This means that the resilient members can be tailored to specific bending requirements and can be achieved in a number of ways; the disclosure should not be seen as being limited to any particular examples.

By way of example, however, at least one (or all) of the one or more resilient members may comprises a variable thickness and/or cross-sectional profile along its length. This means that the strength and/or stiffness and/or resilience of the resilient members could be varied by modifying the thickness and/or cross-sectional profile along their length.

The use of resilient members having a variable strength and/or stiffness and/or resilience in a longitudinal direction is seen as advantageous in its own right, and so from an aspect the present invention provides a support structure for a chair or bed that has a plurality of (e.g., at least 5, 6, 7, 8, 9 or 10) elongate, resilient members arranged in a parallel array across the support structure as described above, wherein the resilient members are the main supporting element (and/or provide the primary support) for a person or other animal on the support structure and comprise a variable strength and/or stiffness and/or resilience in a longitudinal direction.

For example, in accordance with any of the aspects and embodiments described herein, the cross section (or cross-sectional profile) of the resilient members (e.g., transverse to their longitudinal axis) could vary along their length, wherein a relatively flat and wide cross section (or cross-sectional profile) could be provided along a first portion of the length of the resilient members (e.g., where low bending stiffness is required), and a relatively narrow and high cross section (or cross-sectional profile) could be provided along a second, different portion of the length of the resilient members (e.g., where a high bending stiffness is required).

Another way to vary the strength and/or stiffness and/or resilience of the resilient members along their length would be to vary a section modulus of each of the resilient members in a longitudinal direction. For example, a relatively large section modulus could be provided along a first portion of the length of the resilient members (e.g., where low bending stiffness is required), and a relatively small section modulus could be provided along a second, different portion of the length of the resilient members (e.g., where a high bending stiffness is required).

Another way to vary the strength and/or stiffness and/or resilience of the resilient members along their length would be to vary a density of each of the resilient members in a longitudinal direction. For example, a relatively low density could be provided along a first portion of the length of the resilient members (e.g., where low bending stiffness is required), and a relatively high density could be provided along a second, different portion of the length of the resilient members (e.g., where a high bending stiffness is required).

The above methods of varying the strength and/or stiffness and/or resilience of the resilient members could be combined, such that any or all of the approaches could be used, for example a density and cross-sectional profile may be varied in the longitudinal direction.

In the case of a bed, the cross-sectional profile and/or section modulus and/or density of the resilient members could be tailored to the weight distribution of a typical person. For example, the resilient members may have a cross-sectional profile and/or section modulus and/or density in a central longitudinal portion (e.g., the second section or seating area described below, corresponding to the upper legs and buttocks) that provides a relatively low bending stiffness as compared to other longitudinal portions of the resilient members, such as outside of the central longitudinal portion.

In accordance with aspects of the invention, there is provided a system comprising one or more resilient members as described above in combination with a control system. The system may comprise a support structure and/or device as described above comprising the resilient members. The control system may be operatively connected to each of the one or more sensor elements and configured to measure an electrical response from each of the one or more sensor elements, and output a signal including data concerning the movement of the resilient members based on the measured electrical response.

The control system may further comprise one or more sensors, each sensor being operatively connected to one of the one or more sensor elements, and configured to detect an electrical response from the respective sensor element and output a signal indicative of the electrical response.

The control system may further comprise a computer configured to receive the signal(s) from the sensor(s) and process them to output information relating to changes in movement of the resilient members, for example changes in movement due to changes in one or more of pressure, acceleration, strain, or force associated with the resilient member(s). The computer may comprise a processor configured to receive the signal(s) from the sensor element(s) and carry out the processing described above.

The system may further comprise a monitoring apparatus configured to receive the information concerning the movement of the resilient members and determine and output one or more corrective actions based on the information. The one or more corrective actions may comprise raising an alert signal and/or sounding an alarm.

The support structure may comprise a plurality of sections, wherein each section is movable relative to the other sections, and movement of each section is controlled by the control system, and the one or more corrective actions may comprise one or more signals to instruct the control system to move one or more of the sections of the bed.

The apparatus may be a structure configured to support a human or other animal, and the system may further comprise a bed, wherein the support structure is a support structure of the bed.

BRIEF DESCRIPTION OF THE DRAWINGS

Various embodiments will now be described, by way of example only, and with reference to the accompanying drawings in which.

DETAILED DESCRIPTION

Various aspects of the present invention are directed to a support structure for a device. In various embodiments, the device is a bed. The bed may be a medical (e.g., hospital) bed upon which a patient lies, for example to recover from an illness or surgery.

Non-medical applications are also contemplated and intended to fall within the broadest aspects of the invention as described herein. As such, references to "patient" and "caregiver" herein are not intended to limit the embodiments to medical applications, and the terms "patient" and "caregiver" are interchangeable with any terms that refer to a person that might lie on, use or operate the bed as appropriate, for example "user", "controller" or "operator".

Figure 1A:
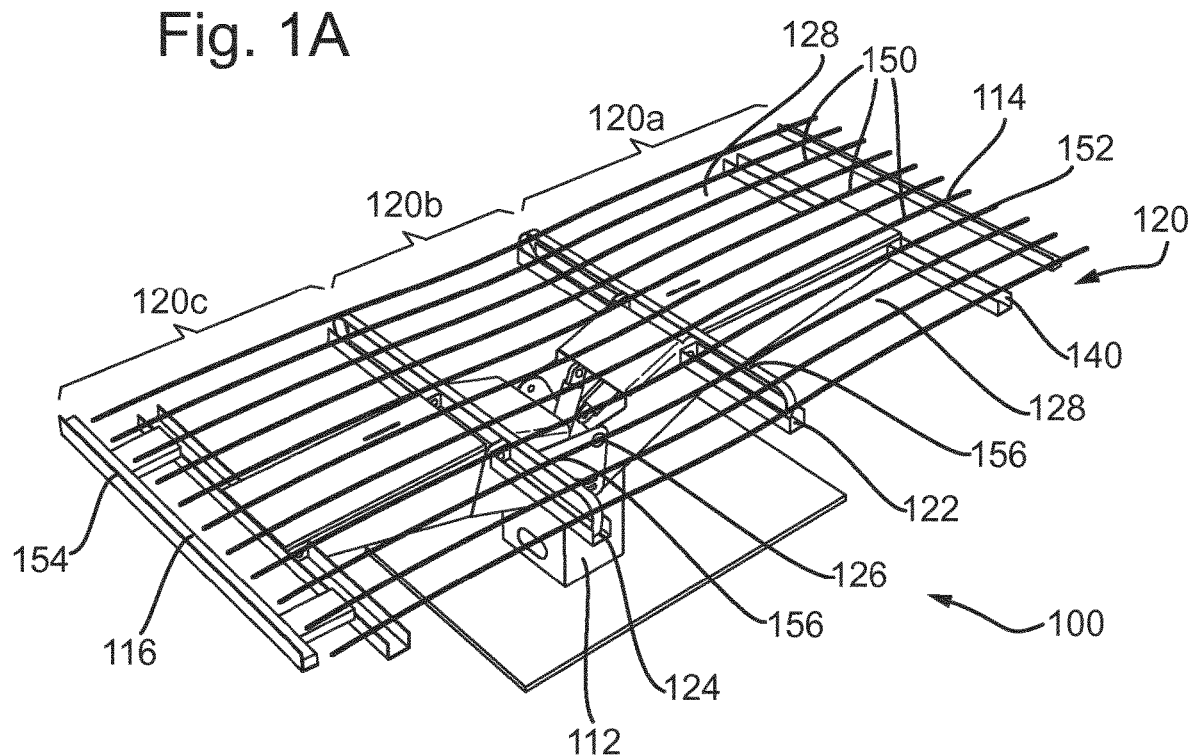
FIG. 1A shows a support structure for a bed in accordance with an embodiment of the present invention.
Figure 1B:
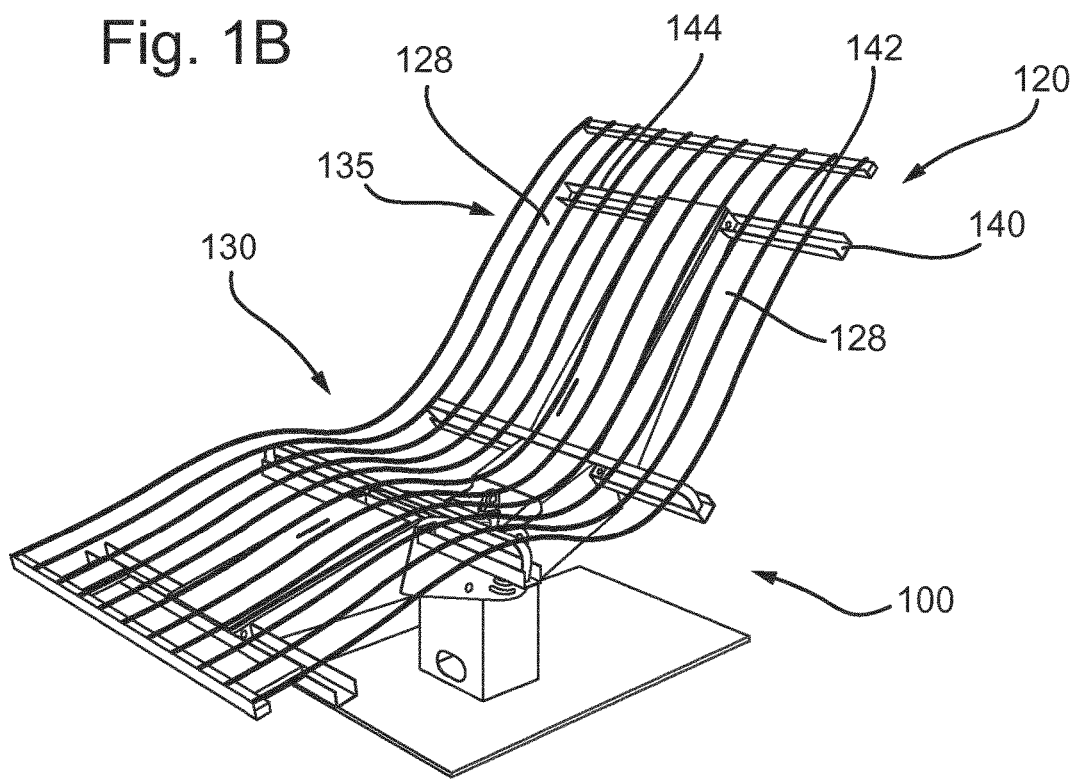
FIG. 1B shows the support structure of FIG. 1A having moved from a flat orientation to an upright orientation.

An example of a support structure 120 will now be described with reference to FIGS. 1A-1B. In the illustrated embodiment the support structure 120 is shown as forming part of a bed 100, although as described above and elsewhere herein the features of the support structure 120 may be used in other applications, such as a seat or other support device.

The support structure 120 comprises a plurality of sections 120a, 120b, 120c each configured to support a respective part of a patient's body. In the illustrated embodiment of FIG. 1A a first section 120a is configured to support a patient's upper body, including the back and head, a second section 120b is configured to support a patient's upper legs and buttocks, and a third section 120c is configured to support a patient's lower legs.

The first section 120a may have a length of between about 0.7-1.1 m, optionally about 0.8 m. The second section 120b may have a length of between about 0.4-0.5 m, optionally about 0.45 m. The third section 120c may have a length of between about 0.5-0.6 m, optionally about 0.55 m. The length may correspond to the lengthwise or longest dimension of the support structure 120. The support structure 120 may extend along the entire length of the bed 100.

Each section may be separated from an adjacent section by a transverse separation line (e.g., a pivot point) 122, 124. A first separation line 122 may separate the first section 120a from the second section 120b, and a second separation line 124 may separate the second section 120b from the third section 120c. The first and second separation lines 122, 124 may correspond to the major points of flexure of a human, as discussed above, namely the knees and waist. A crossbeam or lateral support bar may be located at each of the first and second separation lines 122, 124.

A central pivot point 126 may be located at approximately the centre of the bed 100, for example at the point at which a bed support 112 meets the support structure 120, such that the support structure 120 of the bed 100 can rotate as a whole about the central pivot point 126. The central pivot point 126 may not necessarily be located at a point of flexure, and/or may be located at a point between the first and second separation lines 122, 124.

The support structure 120 may have a length equal to or greater than about 1.5 m, about 1.6 m, about 1.7 m, about 1.8 m, about 1.9 m, about 2.0 m, about 2.1 m, about 2.2 m or about 2.3 m. The length may correspond to the lengthwise or longest dimension of the support structure. The support structure 120 may extend along the entire length of the bed 100.

The support structure 120 may have a width equal to or greater than about 0.8 m, 0.9 m, about 1 m or about 1.1 m. The width may correspond to a direction perpendicular or transverse to the length.

The support structure 120 may be raised from the ground by a height of between about 0.1-1 m, about 0.2-0.9 m, about 0.3-0.9 m, or about 0.5-0.9 m.

In accordance with the invention, the support structure comprises a plurality of resilient members 150, which may comprise an elongate member (for example in the form of a tube or tubular member), wherein one or more sensor elements may extend along the length of the member to allow measurement of changes in movement due to changes in one or more of pressure, acceleration, strain, or force associated with the elongate member. Although the main focus of this invention is the use of sensor elements extending along the length of the support structure, in various embodiments the resilient members are seen as advantageous in their own right and the sensor elements may be omitted.

The resilient members 150 may each comprise a sensor element that is attached to and runs at least partially along the length of the respective resilient member 150. Each of the sensor elements is configured to provide an electrical response proportional to the amount of movement of the respective resilient member. For example, the sensor elements may be configured to generate an electrical charge, current or voltage resulting from a mechanical force applied to the respective resilient member 150. The charge, current or voltage may be proportional to the amount mechanical force applied to the resilient member 150.

The plurality of resilient members 150, for example springs may extend in the longitudinal (i.e., lengthwise or longest) direction from an upper end 114 of the support structure 120 to a lower end 116 of the support structure 120. The resilient members 150 may be held in place at (e.g., attached to) the upper end 114 by an upper holding member 152, and at the lower end 116 by a lower holding member 154. For example, the resilient members 150 may be attached or connected (e.g., welded) to the upper and lower holding members 152, 154.

The resilient members 150 may be attached to further holding members 156 at each separation line. For example, the resilient members 150 may be attached or connected (e.g., welded) to the further holding members 156, for example to the crossbeams or lateral support bars that are located there (if provided).

The resilient members 150 may be configured to support a patient lying on the support structure 120 and/or may provide the primary support for a patient. While it is envisaged that a further material (e.g., a mattress, foam or memory foam, which is not shown in FIGS. 1A-1B) may be provided above (or itself encase) the resilient members 150, the shape and/or profile of the support structure 120 may be determined by the shape and/or profile of the resilient members 150, as shown in more detail in FIG. 2B. The shape and/or profile of the resilient members 150 may also correspond to the shape and/or profile of the sensor elements.

The various sections of the support structure 120 may be independently movable (e.g., up and down) and/or rotatable about their respective separation lines 122, 124. As the various sections of the support structure 120 rotate the resilient members 150 may be configured to change shape. In other words, the resilient members 150 may be biased so as to form a predefined shape and/or profile upon rotation of the various sections of the support structure 120. The shape and/or profile of the resilient members 150 (and therefore the support structure 120) may be different in each section.

Figure 2A:
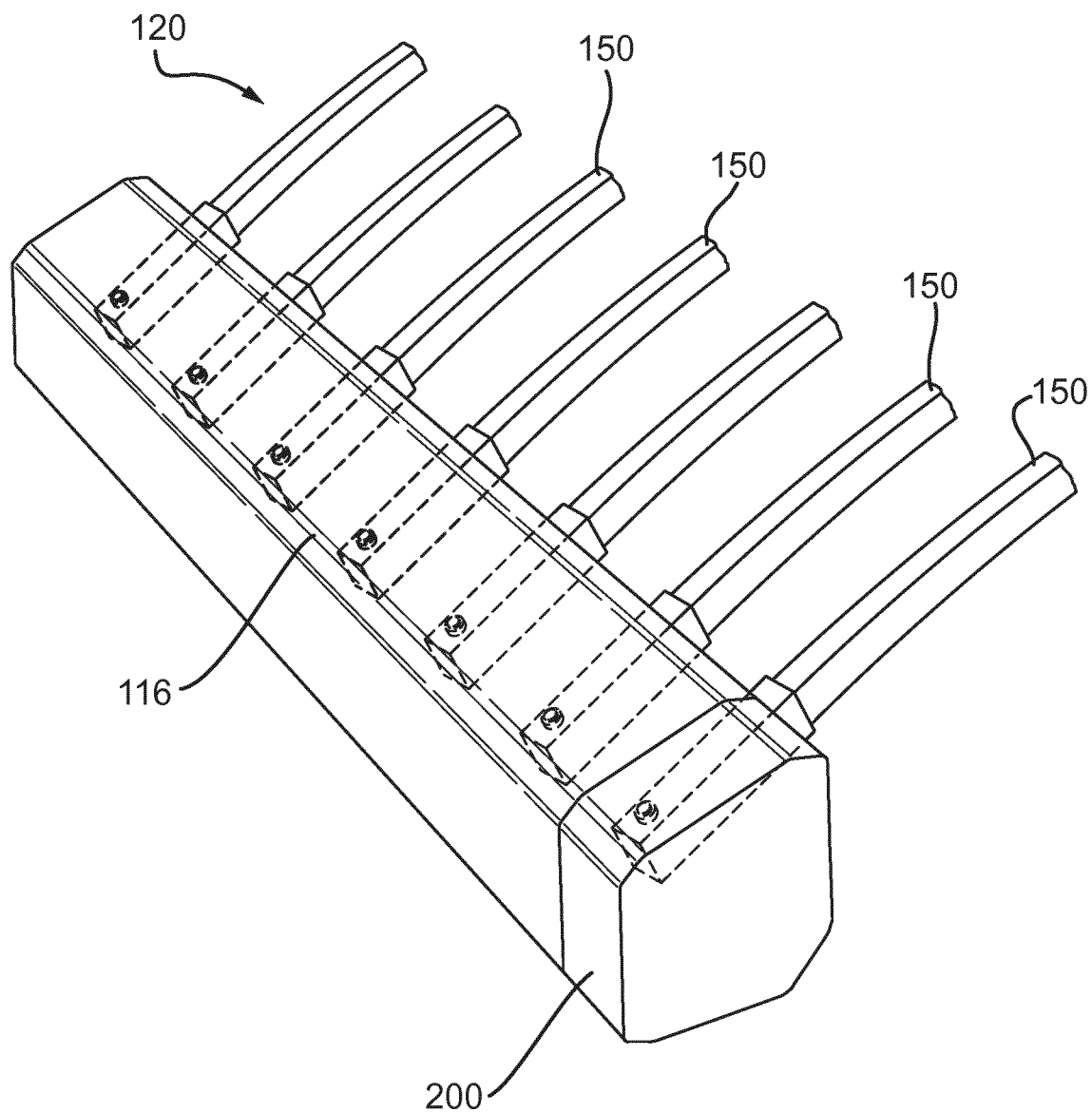
FIG. 2A shows in more detail the connection of resilient members of the support structure of FIG. 1A.
Figure 2B:
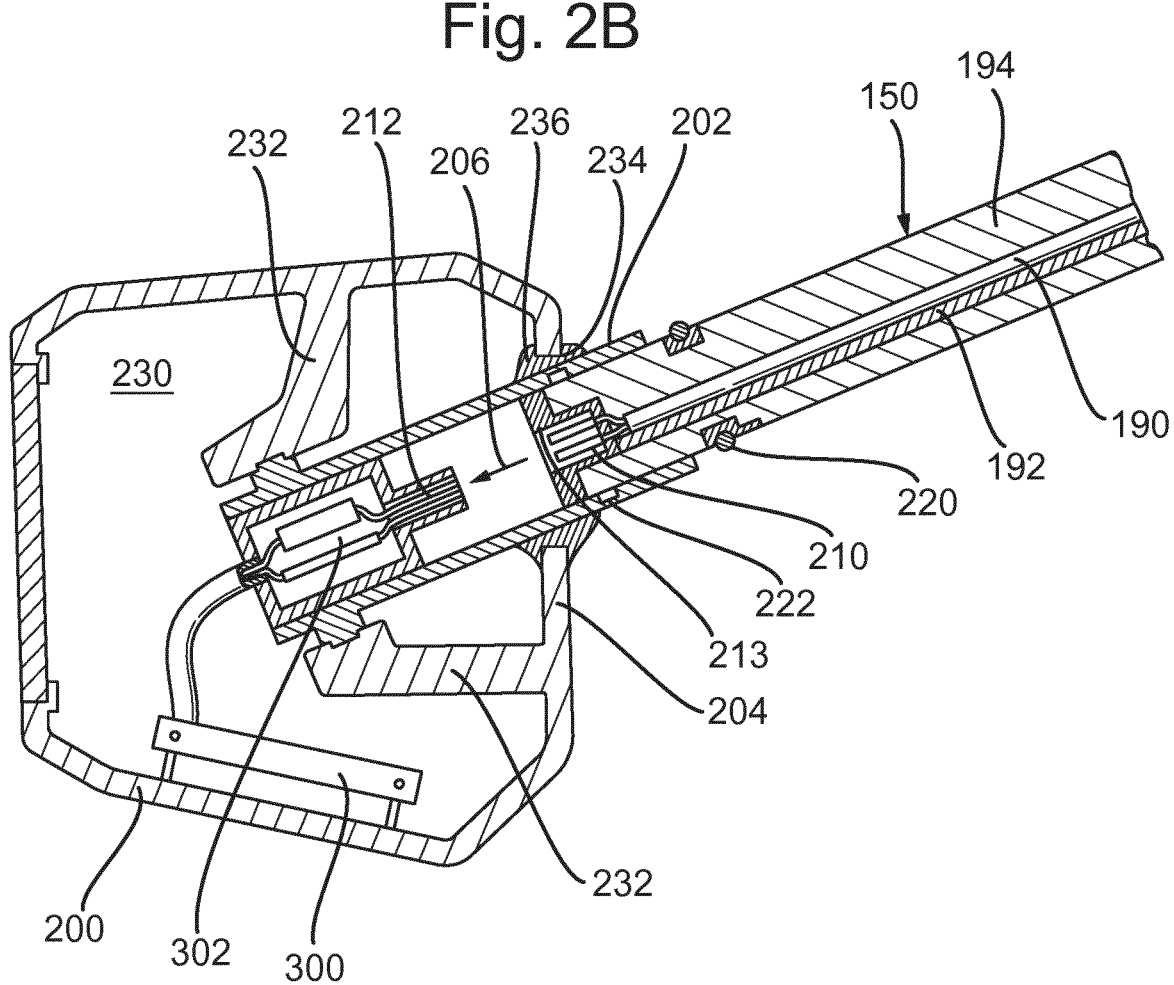
FIG. 2B shown further detail of the connection shown in FIG. 2A.

As shown in the illustrated embodiment of FIG. 2B, upon rotation of the first section 120a about the first separation line 122, and/or the third section 120c about the second separation line 124, the resilient members 150 may be configured to form a convex profile in the first section 120a and/or the third section 120c respectively, and may be configured to form a concave profile in the second section 120b.

References to "concave" and "convex" as used herein should be interpreted as being towards a person (e.g., patient) lying on the bed and in the longitudinal direction, for example such that a concave profile forms a depressed portion (e.g., a dip or valley) of the bed in a longitudinal direction, and a convex profile forms a raised portion (e.g., a bump or protrusion) of the bed in a longitudinal direction.

For example, upon rotation of the sections 120a and 120b from a flat position (as shown in FIG. 2A) into a more upright position (as shown in FIG. 2B) the support structure 120 automatically provides a concave profile 130 (e.g., a pit or valley) as well as a convex profile 135 for lumbar support. The use of longitudinal resilient members 150 (as opposed to vertical springs or lateral members) allows such profiling to be more easily tailored for an intended use of the bed.

The resilient members 150 may be configured, in the flat and upright positions of the support structure 120, to substantially conform to the shape of the body. For example, when the support structure 120 is in a flat position the resilient members 150 may preferably undulate to follow the contour of a body in a lying down position, or less preferably the resilient members 150 may be flat. When the support structure 120 is in an upright position, the support structure 120 may undulate to follow the contour of a body in a seated position. It will be appreciated that the undulations in the resilient members 150 when the support structure 120 is in the seated position may be more pronounced than the undulations in the resilient members 150 when the support structure 120 is in the flat position.

There may be no lateral resilient members or springs provided in the support structure 120. The resilient members 150 may have a length equal to or greater than about 1.5 m, about 1.6 m, about 1.7 m, about 1.8 m, about 1.9 m, about 2.0 m, about 2.1 m, about 2.2 m or about 2.3 m. The length may correspond to the lengthwise or longest dimension of the support structure.

The support structure 120 may comprise at least 5, 6, 7, 8, 9, 10, 15 or 20 resilient members 150 (e.g., in a parallel array) and/or the resilient members may be spaced apart by less than 5, 10, 15 or 20 cm, to provide sufficient support to a person lying on the bed 100.

In accordance with the invention one or more sensor elements may be connected to one or more (or all of) the resilient members 150, which sensors may be configured to provide an electrical response proportional to the amount of movement of the respective resilient member as described above.

For example, the sensor elements may be a piezoelectric material that runs along the length of each respective resilient member 150, to measure the piezoelectric (i.e., electrical) response therefrom.

It will be appreciated that a piezoelectric response of such sensor elements will be at a minimum (or zero) when there is no movement in the resilient members 150, and will increase upon increased movement of the resilient members 150. For example, there may be a very high tension in the resilient members 150, but the piezoelectric response from them may still be at a minimum (or zero). Thus, the use of piezoelectric resilient members 150 is seen as a particularly advantageous development over merely measuring, e.g., tension, since it gives an improved response to and/or more information regarding the movement of a patient being supported on the support structure 120. This is particularly the case when the sensor elements are attached to (e.g., embedded in or encased by) the resilient members forming the primary support for the support structure, since they will respond directly to movement of the resilient members. This is in contrast to conventional arrangements that incorporate a pad within a mattress for example, but do not attach the sensor elements to the resilient members of the mattress that provide primary support (e.g., the mattress springs).

More generally, the use of sensor elements that run along at least part of the length of the resilient members leads to a desirable trade-off, as discussed above. That is, the sensor elements disclosed herein can respond to changes in movement, e.g., a patient moving from one side to another, or having a seizure/sneezing/coughing, etc., as well as smaller movements such as breathing, heart rate fluctuations, abdomen noises and so forth.

The sensor elements also permit fast and simple detection of sudden changes in movement, which in the case of a bed may be caused by a patient as they are about to fall off the bed (for example). The use of a resilient member 150 as disclosed herein (i.e., comprising a sensor element running through or along it) means that a caregiver response (or a response that uses the movement of the support structure 120) can be faster.

The movement in each resilient member 150 could be monitored by a control system that incorporates sensors configured to measure the electrical (e.g., piezoelectric) response from the sensor elements. If the control system is also capable of moving the portions of the bed, then an automatic response to the movement of the resilient members 150 can be provided.

For example, if it becomes apparent that the patient is moving towards the side of the bed, for example due to the various movements of the resilient members 150 that are spaced laterally across the bed, a control system may determine that the patient is about to fall off the bed, and take corrective action. In this example, the combination of resilient members 150, and their spacing laterally across the support structure 120 (e.g., as shown in FIGS. 1A-1B) is seen as particularly advantageous when combined with a control system as described above.

The control system may be configured to sound an alarm or otherwise alert a caregiver (or other person) prior to the patient actually falling off the bed. In embodiments where the bed comprises one or more movable portions, the control system may move (e.g., raise) a suitable portion of the bed in order to prevent the person falling off.

The movement in the resilient members 150 could be monitored over time by the control system. Based on the change in the movement in the resilient members 150 over time the control system may determine movement patterns of the patient, some of which may lead to an alert.

For example, if the electrical (e.g., piezoelectric) response from the sensor elements is substantially stable, and/or follows a normal pattern then the control system may determine that the patient is stable and/or moving normally and continue monitoring. If the movement becomes unstable, and/or follows an abnormal pattern (e.g., due to the patient thrashing or writhing) then the control system could sound an alarm or otherwise alert a caregiver (or other person).

In some embodiments the resilient members 150 and the sensor elements connected thereto may extend along the entire length of the bed. In other embodiments the sensor elements may extend partially along the length of the resilient members 150, for example the portion of the resilient members corresponding to the torso of a person.

Various parts of the support structure 120 may be movable or rotatable in order to provide further automated movement possibilities for a patient, in addition to the rotation about the first and second separation lines 122, 124, and/or the central pivot point 126.

For example, the upper corners 128 of the support structure 120 may be adjustable such that they can be raised or lowered independently of each other and/or the other parts of the support structure 120. This can provide a movement configured to lift the shoulder of a patient lying on the bed.

To effectuate such movement a support bar 140 may be located at or near the upper end 114 of the support structure 120. The support bar 140 may comprise a left arm 142 and a right arm 144, both of which may be independently raised or lowered. One or more motors (not shown) may be provided to raise and lower each of the left arm 142 and right arm 144.

A similar arrangement may be placed at the lower end 116 of the support structure 120 in order to raise and lower the legs or feet of a patient lying on the bed.

Other movements are envisaged. The support structure 120 may be configured such that it can be raised and/or lowered about a longitudinal axis of rotation, for example the central longitudinal axis of the support structure 120. For example, each separation line may comprise a support bar similar to the support bar 140, wherein the support bars may be configured to simultaneously raise all of the right or left arms, so that one half of the support structure 120 is raised. Such a movement may assist in turning a patient.

In various embodiments, the support structure 120 may comprise a plurality of sections (e.g., at least three sections and/or similar to the sections 120a, 120b, 120c), and all or part of the sections may be movable by a translating means, e.g., other than rotation about a pivot point. For example, each section may be movable (e.g., up and down) independently of the other sections. Additionally, or alternatively, a portion of each section may be movable (e.g., up and down) independently of the rest of the section, and/or independently of the other sections.

The portion of each section may be independently movable by configuring the resilient members 150 such that each resilient member 150 is independently movable within that portion of the section. For example, separate actuators could be provided for each resilient member 150 that may be configured to move the resilient member 150 up and down within a particular section, or within a portion of a particular section.

Figure 2C:
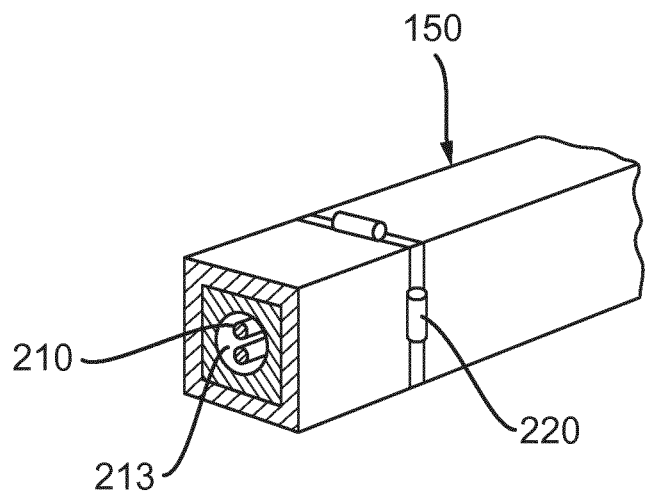
FIG. 2C shows a resilient member of the support structure in isolation.

FIGS. 2A-2C shows in more detail the connection of the resilient members 150 with the lower end 116 of the support structure 120. These embodiments depict a sensor element in the form of a piezoelectric material, but as discussed above and herein any suitable sensor element could be used that fulfills the functionality of the invention.

As shown in FIG. 2A, the lower end 116 of the support structure 120 comprises a bracket 200 that extends laterally across the support structure 120, wherein each of the resilient members 150 plug into the lateral bracket 200 and are substantially fixed in position with respect thereto.

The bracket 200 is shown in more detail in FIG. 2B, which is a cross-sectional view through one of the resilient members 150 and the bracket 200 at the point at which the resilient member 150 connects to the bracket 200.

The resilient member 150 may be inserted into a housing 202 that extends through an outer wall 204 of the bracket 200. The housing 202 is configured to receive the resilient member 150 in a sliding engagement, such that the resilient member 150 may be inserted into the housing in the direction of arrow 206 until male connectors 210 located on the resilient member 150 mate with cooperating female connectors 212 located within the housing 202. The male connectors 210 located on the resilient member 150 may be operatively and/or electrically connected to the sensor element that runs through the resilient member 150, e.g., a piezoelectric element 190 as described below.

The housing 202 may comprise an elongated hollow tube having internal dimensions that substantially match the external dimensions of the resilient member 150, such that an interference fit may be provided between the resilient member 150 and the housing 202.

To further secure the connection between the resilient member 150 and the housing 202, a snap fit mechanism may be used. The snap fit mechanism may comprise male engaging elements 220 that are located on the outer surface of the resilient member 150, as well as female engaging elements 222 located on the inner surface of the housing 202. These may cooperate once the resilient member 150 is inserted into the housing 202 such that the male connectors 210 are sufficiently mated with the female connectors 212, to provide a snap fit between the resilient member 150 and the housing 202.

The housing 202 may be held within an interior cavity 230 of the brackets 200 through the use of one or more flanges 232, which may be configured to hold the housing 202 in position. Furthermore, the housing 202 may extend through an aperture 234 in the outer wall 204 of the bracket 200. In various embodiments, an elastic or other deformable material 236 may be located between the housing 202 and the surfaces of the aperture 234, to allow the housing 202 to flex, which may be beneficial due to the movement of the resilient members 150 in use.

The female connectors 212 may be connected to a control system 300 via one or more electronic components, which may include a sensor 302 configured to measure the electrical response from the sensor elements within the resilient members 150 (as discussed above). The control system 300 may be a computer, for example a single board computer.

In various embodiments, the control system 300 may be located remotely from the support structure 120, rather than incorporated within the structure of the bracket 200 as shown in FIG. 2B. In these situations, a suitable connection (e.g., a wired or wireless connection) would be required between the electronic components 302 and the control system 300.

In the illustrated embodiment, the resilient members 150 may only be required to connect to suitable electronics (e.g., the sensor 302 and/or the control system 300) at one end of the bed, namely the lower end 116. This is because the electrical (e.g., piezoelectric) response of the sensor elements can be measured at one end thereof, and is not required to be measured at both ends of the resilient members 150. Of course, in various embodiments a bracket may be provided at the upper end 114 of the support structure 120 which is similar to the bracket 200 shown in FIG. 2B. This could be used to provide an additional, or alternative measurement location of the piezoelectric response from the resilient members 150.

It will be appreciated that each resilient member 150 may have a respective housing 202 that connects it to a respective sensor 302, and then each sensor 302 could communicate with the control system 300 to provide the functionality described herein.

FIG. 2B also shows the internal features of the resilient members 150, including a sensor element, e.g., a piezoelectric element 190 that extends axially along the length of the resilient member 150. The male connectors 210 described above connect to the piezoelectric element 190 such that the electric (e.g., piezoelectric) response from the piezoelectric element 190 can be measured.

Located adjacent to the piezoelectric element 190 may be a material 192 configured to provide stiffness (if necessary) to the resilient member 150, for example a composite material. Located around the piezoelectric element 190, and the composite material 192 (if present) is an outer sheath 194, for example an elastomeric material such as polyurethane ("PU", "PUR"). In various embodiments, the piezoelectric element 190 may be encased by the outer sheath 194, such that the piezoelectric element 190 is contained completely within the outer sheath 194. This protects the piezoelectric element 190 in use.

FIG. 2C shows a perspective view of the resilient member 150 in isolation. In this embodiment, the resilient member 150 has a substantially square cross-sectional profile, although any suitable profile may be used, e.g., circular, triangular, etc. The male engaging elements 220 of the snap fit mechanism can be seen located in the outer surface of the resilient member 150. In addition, the male connectors 210 of the resilient member 150 can be seen embedded in a cavity 213 at one axial end of the resilient member 150.

As will be appreciated from FIG. 2B, the female connectors 212 insert into the cavity 213 containing the male connectors 210 to provide the piezoelectric sensing as described herein. However, these illustrations are only exemplary, and any suitable connection between the piezoelectric element 190 and the sensor 302 may be used to provide this functionality.

General refinements of the resilient members will now be described. These refinements may be provided with respect to the resilient members 150 shown and described in respect of the support structure 120. However, the refinements will be generally applicable to any of the resilient members described herein, and are not limited to the illustrated embodiments, for example. The features of the refinements may also be combined in as much as they are compatible with each other.

Generally the resilient members are made up of a sensor (e.g., piezoelectric) element, a resilient material, and a further (e.g., composite) material having a high tensile strength. As discussed above in various embodiments the sensor element may be omitted.

In various embodiments the resilient members could comprise one or more materials intended to impart a particular quality (e.g., stiffness and/or resilience and/or tensile strength). For example, the one or more materials could be one or more of glass reinforced plastic or fiberglass ("GFK"), spring steel, and composite materials.

The resilience and/or stiffness (e.g., bending stiffness) of each of the resilient members may be uniform along the length of the resilient member. Alternatively, the resilience and/or stiffness (e.g., bending stiffness) may vary along the length of the resilient member.

Figure 3A:
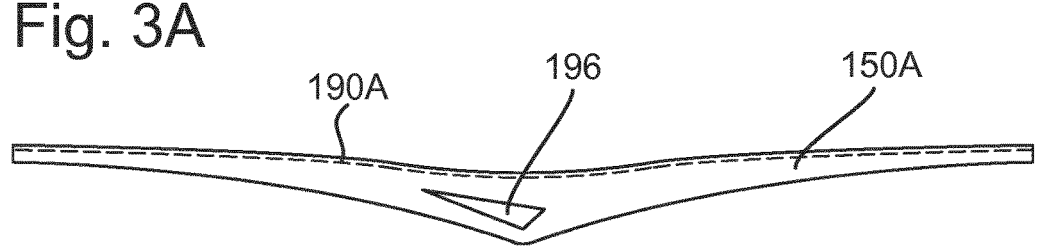
FIGS. 3A-3E show various refinements of the resilient members described herein.

FIG. 3A illustrates an example of how this variation may be provided, in which a resilient member 150A is shown having a varying thickness along its length. The resilient member 150A in this example has a relatively thin portion at either end that extends to one or more relatively thick portions in the centre. One or more apertures 196 may be provided in the resilient member 150A to vary the resilience and/or stiffness further. Of course, any suitable variation of thickness, or provision of apertures may be used to provide a tailored resilience and/or stiffness along the length of the resilient member to meet the requirements of a particular application. For resilient members having a varying thickness, the sensor element (e.g., piezoelectric material 190A) may be provided in the upper portion of the member (i.e., closest to an upper surface configured to face a person or animal in use), and along its entire length, as shown in FIG. 3A. A cross-sectional profile, section modulus or density could also be varied in a longitudinal direction, in order to vary the resilience and/or stiffness of the resilient members described herein.

Figure 3B:
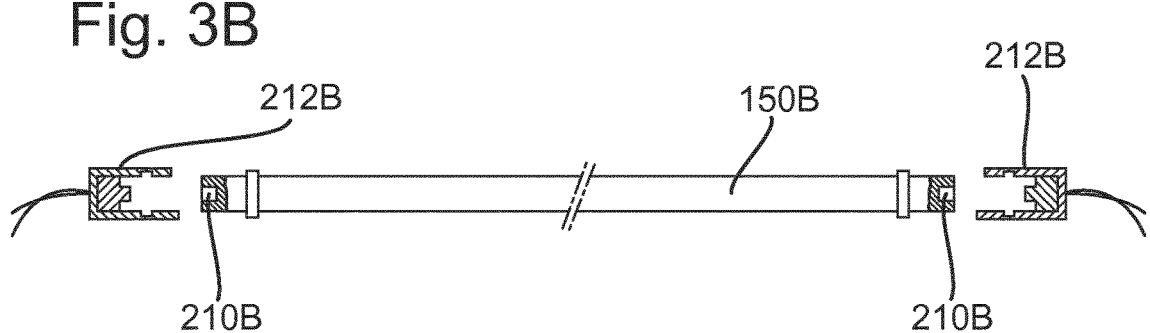

FIG. 3B illustrates an example of how the resilient members may be connected to a control system at either end of the resilient member 150B. That is, the resilient member 150B comprises connecting elements 210B located at each end, which are operatively and/or electrically connected to a sensor (e.g., piezoelectric) element that runs through the resilient member 150B. Each connecting element 210B may connect to a cooperating sensor 212B configured to measure the electrical (e.g., piezoelectric) response of the sensor element that runs through the resilient member 150B. These responses may be transmitted to a common control system, e.g., any of the control systems described herein.

Figure 3C:
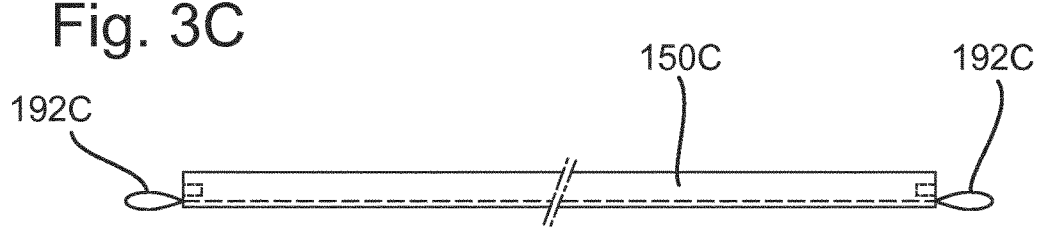

FIG. 3C illustrates an embodiment of a resilient member 150C that comprises end loops 192C that can be used to connect the resilient member 150C to a particular device, for example a device (e.g., a support structure) comprising cooperating hooks.

Figure 3D:
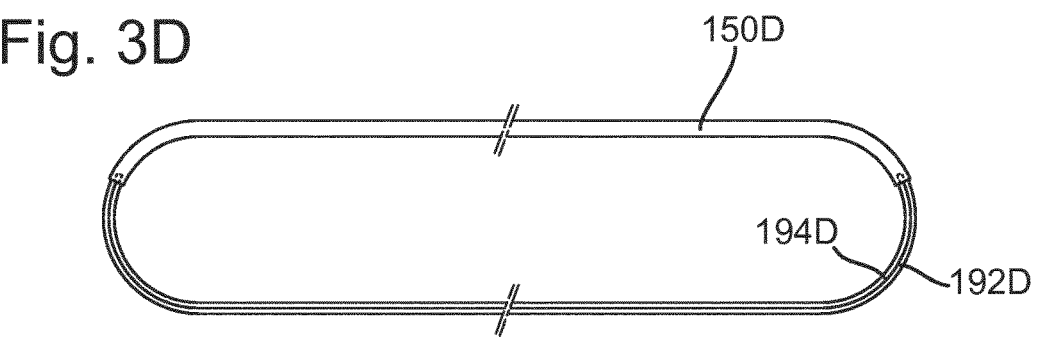

FIG. 3D illustrates an embodiment of a resilient member 150D in which the resilient material 194D and/or composite material 192D extend out from one end of the resilient member 150D, and loops round to connect to the other end of the resilient member 150D so as to form a continuous loop of the resilient and/or composite material. These embodiments may be useful where the resilient member 150D forms part of a moving support structure, such as a conveyor belt. A suitable sensor may be connected to the resilient member 150D at any suitable location.

Figure 3E:
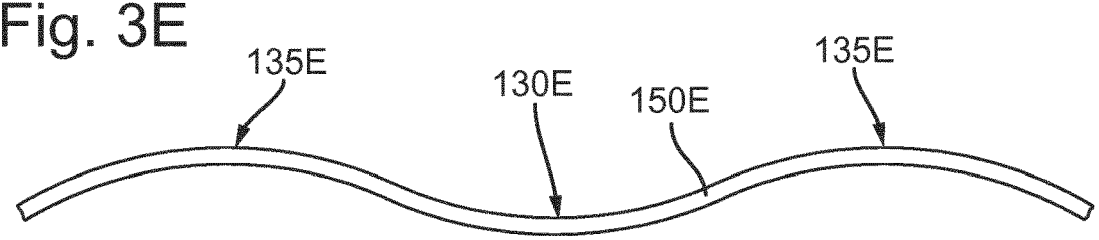

FIG. 3E shows a resilient member 150E that is provided having a predefined shape, in this case a wavy shape having a concave portion 130E, as well as one or more convex portions 135E. It is envisaged that the resilient members could be provided having any suitable predefined shape to suit a particular application, for example the shape depicted in FIG. 1B in respect of support structure 120.

Figure 4A:
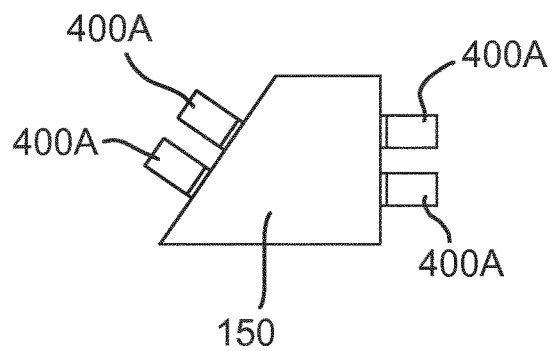
FIGS. 4A-4C show various possible cross-sections of the resilient members described herein.
Figure 4B:
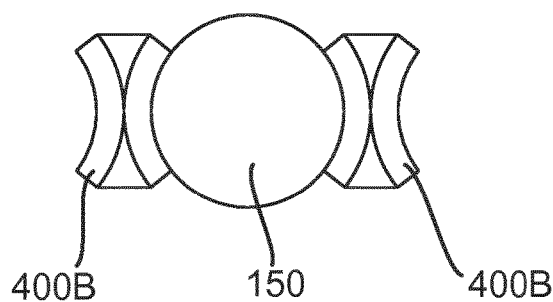
Figure 4C:
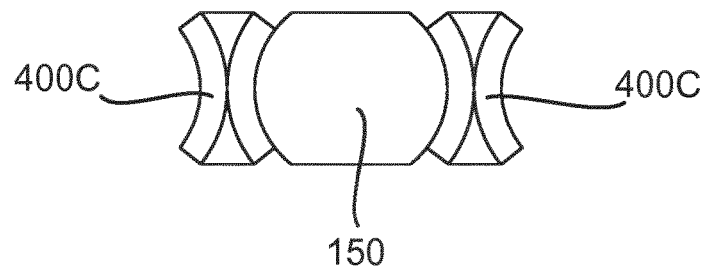

FIGS. 4A, 4B and 4C illustrate three different examples of cross sections that the resilient members 150 may have.

FIG. 4A illustrates a trapezoidal cross-section, with suitable thrust bearings 400A along which the resilient member 150 can slide in use. The thrust bearings 400A in FIG. 4A are shown as located on opposed sides of the resilient member 150.

FIG. 4B illustrates a resilient member 150 having a circular cross-section, as well as suitable thrust bearings 400B. As can be seen in FIG. 4B, the thrust bearings 400B have a concave profile that faces the resilient member 150, such that the curved outer surface of the resilient member 150 matches the concave profile of the thrust bearings 400B. This means that the resilient member 150 is securely held within the thrust bearings 400B, but can also move adequately, e.g., by rotation about the longitudinal axis of the resilient member 150, or translation along this axis.

FIG. 4C illustrates a resilient member 150 having a substantially oval profile, with suitable thrust bearings 400C. The thrust bearings 400C are similar to the thrust bearings 400B shown in respect of FIG. 4B, in that they have a concave profile matching the curved outer surface of the resilient member 150. However, the resilient member 150 comprises substantially flat surfaces that connect the curved surfaces either side of the resilient member 150. Use of flat surfaces gives the spring improved lateral and rotational stability (i.e., keeping the spring in the same orientation from head to toe), using the same guiding members.

Figure 5:
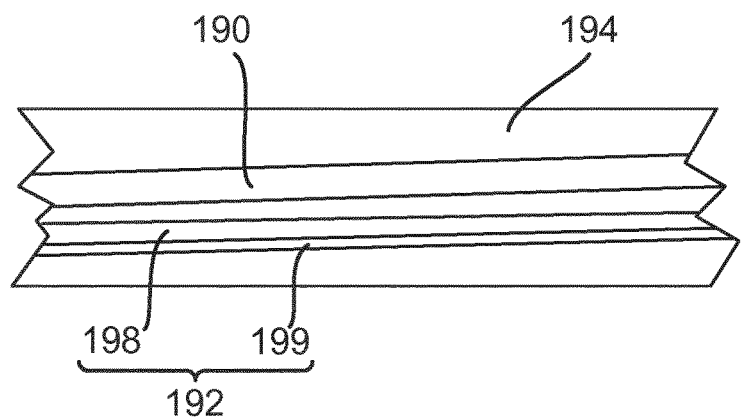
FIG. 5 shows an exemplary structure of a resilient member in accordance with an embodiment of the present invention.

FIG. 5 illustrates a particular cross-section of the resilient member 150, in which the composite material 192 is formed from a first element 198 and a second, different element 199. In various embodiments, the characteristics of the first element 198 and the second element 199 may be varied for particular applications. For example, the first element 198 may be made from a material having a relatively low tensile strength, but relatively high resilience, while the second element 199 may be made from a material having a relatively high tensile strength. In such embodiments, the first material 198 could be glass-reinforced plastic or fibreglass ("GFK") or spring steel, and the second material 199 could be a flat, high tensile wire. An outer sheath 194 is present (as in the embodiment of FIG. 2B) that encases the first element 198 and the second element 199, as well as the piezoelectric element 190.

Figure 6A:
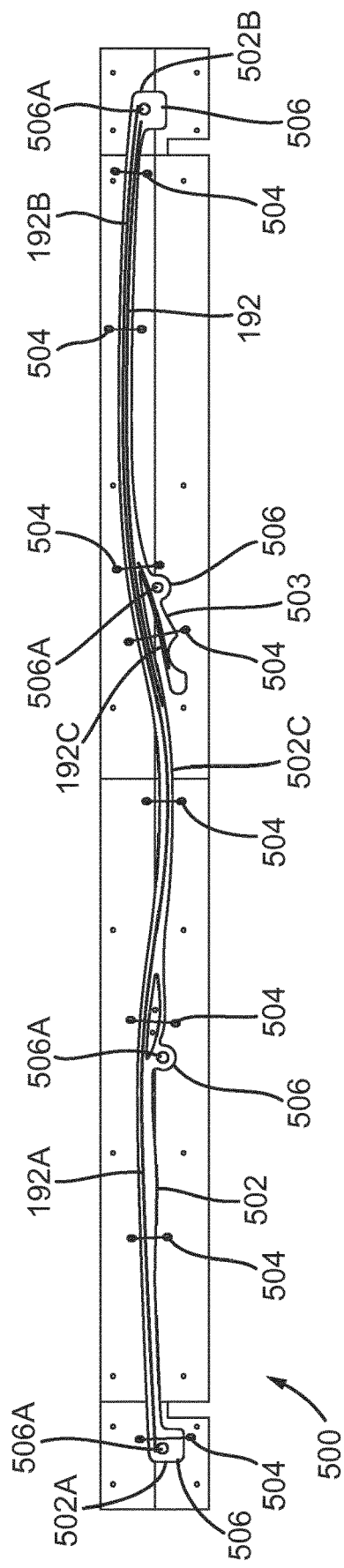
FIGS. 6A and 6B show a mold and resilient member formed from the mold.
Figure 6B:
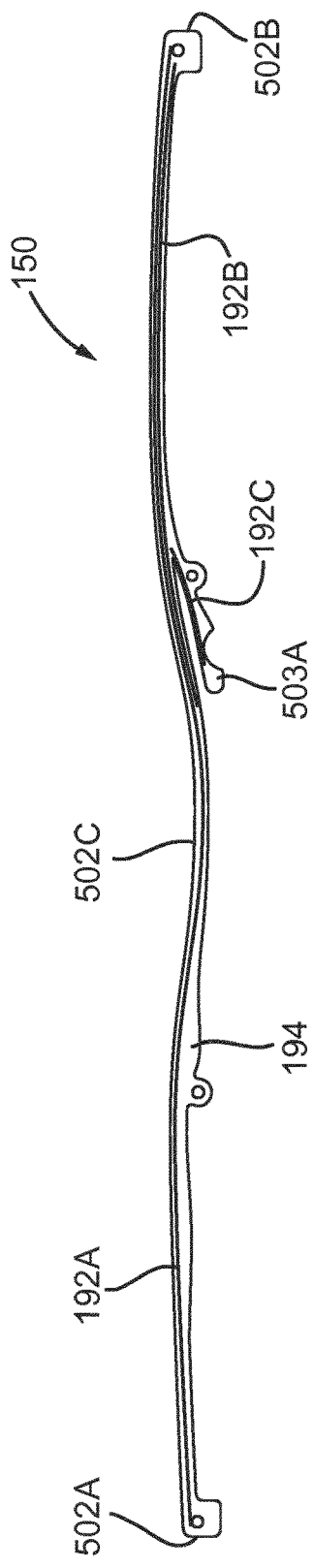

FIGS. 6A and 6B show how a spring according to the present invention may be manufactured.

FIG. 6A shows an apparatus 500 including a central cavity 502 that forms part of a mold configured to receive a material corresponding to the outer sheath 194 (e.g., polyurethane) in liquid form. The central cavity 502 extends from a first end 502A to a second end 502B via a midsection 502C located approximately halfway along the length of the cavity 502. An arm section 503 extends from the central cavity 502 and also comprises part of the mold. The lengths of the various parts of the mold are shown in FIG. 6A, from which relative dimensions of the parts are shown accurately.

The central cavity 502 includes three portions 506 that each correspond to an attachment location where the resilient member will attach to a support structure, for example attachment locations at the separation lines 122, 124 of the bed described above in respect of FIG. 1A or 1B. A further portion 506 may be provided on the arm section 503 that also corresponds to an attachment location. At each of the portions 506 a pin 506A is provided so as to create a hole in the resilient member to allow attachment to a support structure.

The composite material 192 (e.g., "GFK") is provided within the mold and held in place by a plurality of pins 504. In this particular embodiment, 3 strands of the composite material 192 are shown. A first 192A of the strands runs the entire length of the cavity 502, a second 192B of the strands runs from approximately the midsection 502C of the mold to approximately the first end 502A of the mold, and a third 192C of the strands runs along the length of the arm section 503.

Although not shown in FIG. 6A for clarity purposes, a sensor element (e.g., a piezoelectric element 190) as described herein may be attached to the first 192A of the strands that runs the entire length of the cavity 502.

FIG. 6B shows the resilient member 150 formed from the mold of FIG. 6A, in which it can be seen that the outer sheath 194 defines the shape and size of the resilient member 150, whilst the composite materials 192A, 192B, 192C run along the length of the resilient member 150 and into the arm portion 503A formed by the arm section 503 of the mold.

FIG. 6B shows the resting state of the resilient member 150 in this embodiment, and can be seen that there is a concave profile corresponding to the midsection 502C, and a slight convex profile between the midsection 502C and the second end 502B of the resilient member 150. This particular resilient member 150 is usable with a support structure in the form of a bed, wherein the second end 502B corresponds to the end at which a person would rest their head, the midsection 502C corresponds to the portion of the bed where the persons buttocks would rest, and the first end 502A corresponds to the portion of the bed where the person's feet would rest. This profile of a resilient member 150 in its resting state is seen as particularly suitable for such an application. The dimensions of the resilient member 150 shown in FIG. 6B correspond to those of the mold, and relative dimensions of the resilient member 150 are shown accurately.

Although the present invention has been described with reference to preferred embodiments, it will be understood by those skilled in the art that various changes in form and detail may be made without departing from the scope of the invention as set forth in the accompanying claims.

The invention claimed is:

1. A support structure comprising a plurality of elongate, resilient members configured to support a person,
wherein each resilient member extends lengthwise in the direction of the longest side of the support structure, and from a first end at the top of the support structure to a second, opposite end at the bottom of the support structure, wherein elongate is defined in the lengthwise direction of the support structure,
wherein the resilient members each have a central longitudinal axis and a length defined along the central longitudinal axis that is at least 20 times a width of the resilient member, wherein the width is defined as the largest lateral dimension of the resilient member that extends through its central longitudinal axis,
wherein the resilient members are arranged parallel to each other in an array across the support structure,
wherein the resilient members are separated from each other in a lateral, widthwise direction, and are each fixed against lateral (side-to-side) movement towards and away from each other in the lateral, widthwise direction,
wherein the resilient members each comprise a sensor element in the form of a piezoelectric material that is attached to and runs along a length of the respective resilient member such that respective resilient members and sensor elements have parallel longitudinal axes, and each of the sensor elements is configured to provide an electrical response proportional to the amount of movement of the respective resilient member, and
wherein the support structure is not configured as a pad.

2. The support structure of claim 1, wherein the sensor elements are each attached to a respective resilient member, and thereby are configured to generate an electrical charge, current or voltage resulting from any movement of the respective resilient member and such that the charge, current or voltage generated by the sensor element is proportional to the movement of the respective resilient member.

3. The support structure of claim 1, wherein the length is at least 50 times the width of the resilient member.

4. The support structure of claim 1, wherein the sensor elements are each embedded in a groove located in an upper surface of a respective one of the resilient members.

5. The support structure of claim 1, wherein each of the resilient members comprises an outer sheath encasing a respective one of the sensor elements, wherein the outer sheath is formed of a composite material and configured to provide stiffness to the respective resilient member.

6. The support structure of claim 5, wherein each of the resilient members further comprises a resilient support element that runs at least partially along the length of the resilient member parallel with and connected to the respective sensor element, wherein the resilient elements is configured to support the respective sensor element of the resilient member.

7. The support structure of claim 1, wherein the resilient members comprise a variable stiffness along their length.

8. A system comprising:
a support structure comprising:
a plurality of elongate, resilient members configured to support a person,
wherein each resilient member extends lengthwise in the direction of the longest side of the support structure, and from a first end at the top of the support structure to a second, opposite end at the bottom of the support structure, wherein elongate is defined in the lengthwise direction of the support structure,
wherein the resilient members each have a central longitudinal axis and a length defined along the central longitudinal axis that is at least 20 times a width of the resilient member, wherein the width is defined as the largest lateral dimension of the resilient member that extends through its central longitudinal axis,
wherein the resilient members are arranged parallel to each other in an array across the support structure,
wherein the resilient members each comprise a sensor element in the form of a piezoelectric material that is attached to and runs along a length of the respective resilient member such that respective resilient members and sensor elements have parallel longitudinal axes, and each of the sensor elements is configured to provide an electrical response proportional to the amount of movement of the respective resilient member, and
wherein the resilient members do not form part of a pad; and
a computer operatively connected to each of the sensor elements and configured to measure an electrical response from each of the sensor elements, and output a signal including data concerning the movement of the resilient members based on the measured electrical response.

9. The system of claim 8, further comprising a plurality of sensors, each sensor being operatively connected to one of the sensor elements, and configured to detect an electrical response from the respective sensor element and output a signal indicative of the electrical response.

10. The system of claim 8, further comprising the computer configured to receive the information concerning the movement of the resilient members and determine and output one or more corrective actions based on the information.

11. The system of claim 10, wherein the support structure comprises a plurality of sections, wherein each section is movable relative to the other sections, and movement of each section is controlled by the computer, and the one or more corrective actions comprises one or more signals to instruct the computer to move one or more of the sections of the bed, wherein the one or more signals are provided as an automatic response to the movement of the resilient members as measured using the sensor elements.

12. The support structure of claim 1, wherein each resilient member and sensor element form a pair, and the pairs of resilient members and sensor elements each extend in the same lengthwise direction from the first end of the support structure towards the second end of the support structure.

13. The support structure of claim 1, wherein each resilient member extends along the entire length of the support structure.

14. The support structure of claim 1, wherein lengthwise is defined with respect to a central longitudinal axis of the resilient member.

15. The support structure of claim 1, wherein each sensor element extends along an entire length of the respective resilient member.

16. A support structure comprising:
a plurality of elongate, resilient members configured to support a person, and
a bracket that extends laterally across an end of the support structure,
wherein each resilient member extends lengthwise in the direction of the longest side of the support structure, and from a first end at the top of the support structure to a second, opposite end at the bottom of the support structure, wherein elongate is defined in the lengthwise direction of the support structure,
wherein the resilient members each have a central longitudinal axis and a length defined along the central longitudinal axis that is at least 20 times a width of the resilient member, wherein the width is defined as the largest lateral dimension of the resilient member that extends through its central longitudinal axis,
wherein the resilient members are arranged parallel to each other in an array across the support structure,
wherein the resilient members each comprise a sensor element in the form of a piezoelectric material that is attached to and runs along a length of the respective resilient member such that respective resilient members and sensor elements have parallel longitudinal axes, and each of the sensor elements is configured to provide an electrical response proportional to the amount of movement of the respective resilient member,
wherein each of the resilient members are connected to the bracket,
wherein the bracket comprises a plurality of connectors that are each electrically connected to a respective one of the sensor elements, and
wherein the support structure is not configured as a pad.

17. The support structure of claim 1, wherein the resilient members comprise a resilient material and a material having a high tensile strength.

18. The support structure of claim 1, wherein each resilient member is independently movable.

\* \* \* \* \*